United States Patent
Vidlund et al.

(10) Patent No.: US 9,192,363 B2
(45) Date of Patent: Nov. 24, 2015

(54) BIOADHESIVE APPLICATOR AND METHODS OF SEALING TISSUE PUNCTURES USING SAME

(75) Inventors: Robert M. Vidlund, Forest Lake, MN (US); Douglas P. Killion, Maple Grove, MN (US)

(73) Assignee: ST. JUDE MEDICAL, INC., St. Paul, MN (US)

( * ) Notice: Subject to any disclaimer, the term of this patent is extended or adjusted under 35 U.S.C. 154(b) by 407 days.

(21) Appl. No.: 13/106,707

(22) Filed: May 12, 2011

(65) Prior Publication Data

US 2011/0282383 A1 Nov. 17, 2011

Related U.S. Application Data

(60) Provisional application No. 61/334,051, filed on May 12, 2010.

(51) Int. Cl.
*A61B 17/08* (2006.01)
*A61B 17/00* (2006.01)
*A61M 5/19* (2006.01)

(52) U.S. Cl.
CPC ............ *A61B 17/0057* (2013.01); *A61M 5/19* (2013.01); *A61B 2017/0065* (2013.01); *A61B 2017/00495* (2013.01); *A61B 2017/00654* (2013.01)

(58) Field of Classification Search
CPC ................... A61B 17/0057; A61B 17/00491; A61B 2017/0065; A61B 2017/00495
USPC ........ 606/191–194, 213; 604/153; 222/145.4, 222/145.6, 566
See application file for complete search history.

(56) References Cited

U.S. PATENT DOCUMENTS 3,411,534 A * 11/1968 Rose .............................. 137/595
5,782,860 A *  7/1998 Epstein et al. ................. 606/213
(Continued)

FOREIGN PATENT DOCUMENTS

JP    2002025137 A    8/2002
JP    2007530139 A   11/2007
(Continued)

OTHER PUBLICATIONS

PCT International Search Report for PCT International Application No. PCT/US2011/000837, mailed Sep. 19, 2011, (4 pp.).

*Primary Examiner* — Gregory Anderson
*Assistant Examiner* — Christina Lauer
(74) *Attorney, Agent, or Firm* — Holland & Hart

(57) ABSTRACT

A closure device includes a delivery member, a sealing material applicator, and an expandable member. The delivery member is insertable through a tissue tract to a vessel puncture. The sealing material applicator is configured to supply a volume of sealing material to the delivery member and includes first and second multi-chamber devices and a valve assembly. Each chamber of the first and second multi-chamber devices holds a component of the sealing material, and operating the valve assembly permits mixing of at least some of the components prior to connecting the sealing material applicator to the delivery member. The expandable member is positionable within the vessel to temporarily seal closed the vessel puncture from within the vessel. The closure device is operable to deliver the sealing material from the sealing material applicator, through the delivery member, and to the tissue tract to seal closed the vessel puncture from outside the vessel.

23 Claims, 8 Drawing Sheets

(56) References Cited

U.S. PATENT DOCUMENTS

| | | | |
|---|---|---|---|
| 6,045,569 A | 4/2000 | Kensey et al. | |
| 6,090,130 A | 7/2000 | Nash et al. | |
| 7,422,579 B2 | 9/2008 | Wahr et al. | |
| 7,654,978 B2 | 2/2010 | Wahr et al. | |
| 7,867,216 B2 | 1/2011 | Wahr et al. | |
| 8,333,787 B2 | 12/2012 | Pipenhagen et al. | |
| 8,506,592 B2 | 8/2013 | Killion et al. | |
| 2001/0016709 A1* | 8/2001 | Tovey et al. | 604/153 |
| 2003/0225378 A1* | 12/2003 | Wilkie et al. | 604/221 |
| 2005/0027240 A1* | 2/2005 | Fehr et al. | 604/82 |
| 2007/0012724 A1* | 1/2007 | Feinberg et al. | 222/137 |
| 2008/0253987 A1 | 10/2008 | Rehor et al. | |
| 2011/0114212 A1 | 5/2011 | Greter et al. | |
| 2011/0166595 A1 | 7/2011 | Vidlund et al. | |

FOREIGN PATENT DOCUMENTS

| | | |
|---|---|---|
| WO | 0012018 A1 | 3/2000 |
| WO | 2005092204 A2 | 10/2005 |
| WO | 2010012114 A1 | 2/2010 |
| WO | 2010134989 A1 | 11/2010 |

* cited by examiner

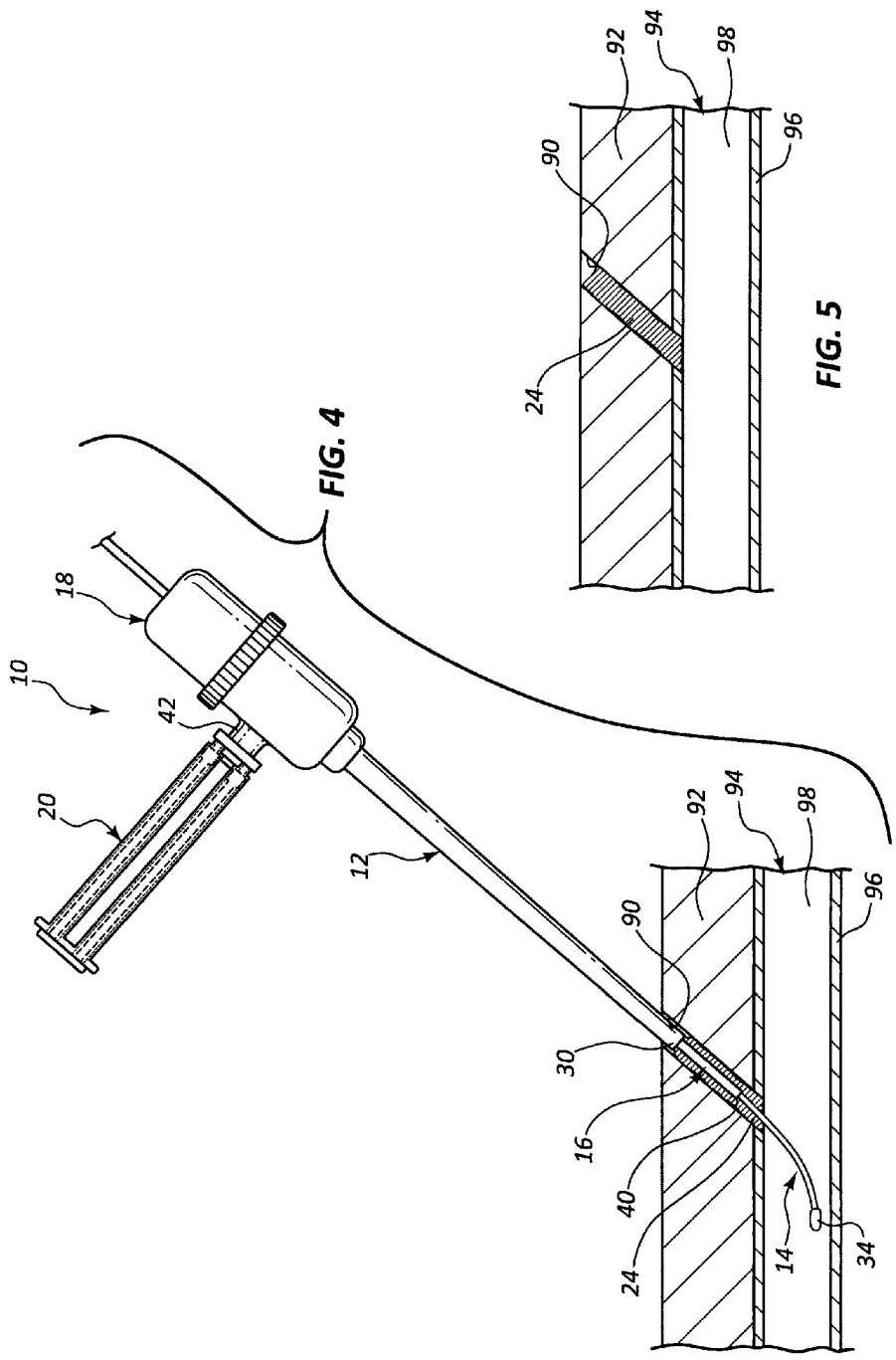

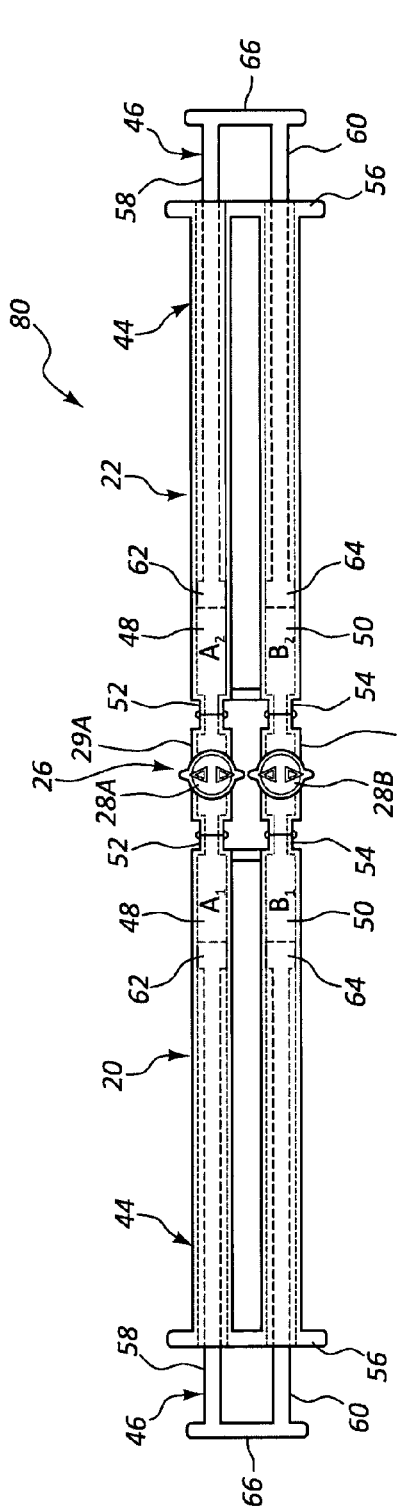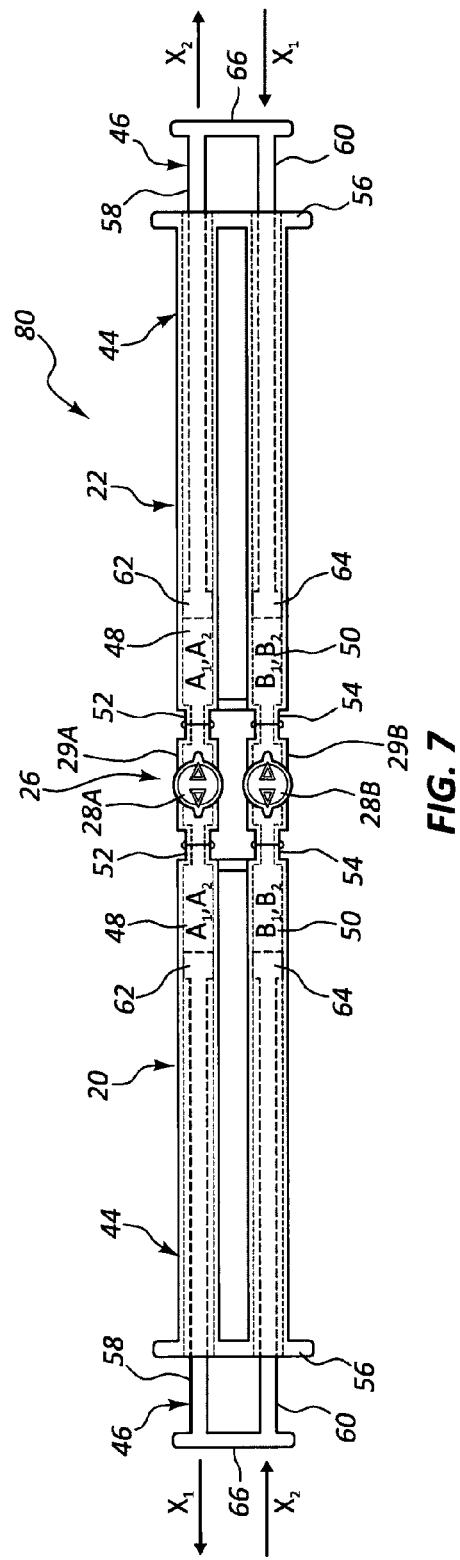

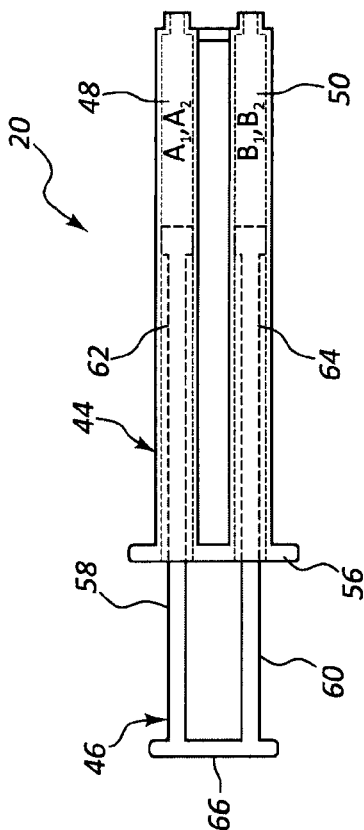
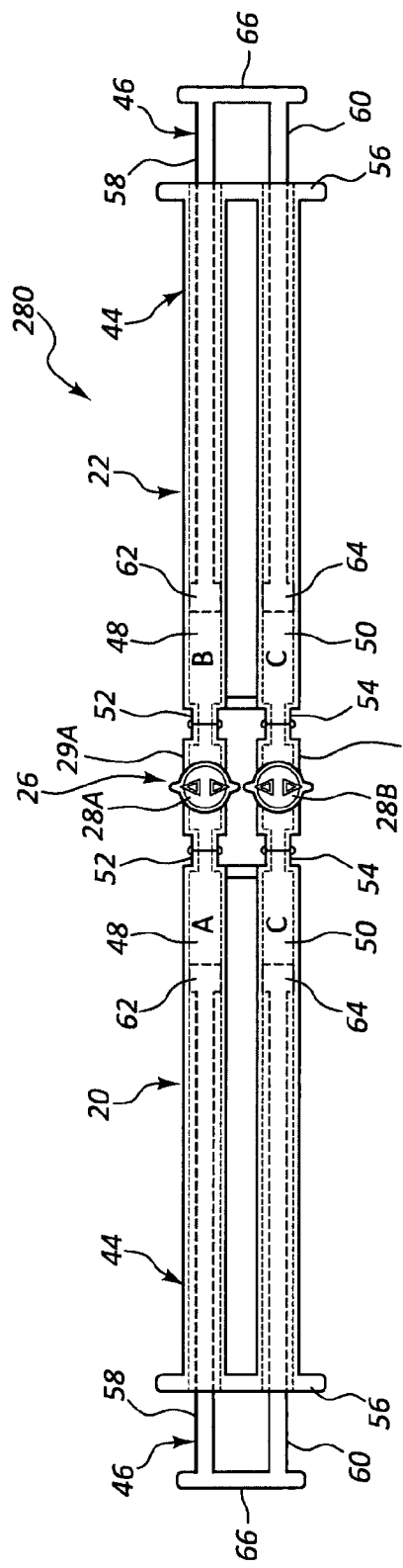

BIOADHESIVE APPLICATOR AND METHODS OF SEALING TISSUE PUNCTURES USING SAME

CROSS-REFERENCE TO RELATED APPLICATION

This application claims the benefit of the filing date of U.S. Provisional Application No. 61/334,051, filed 12 May 2010, and entitled BIOADHESIVE APPLICATOR, the disclosure of which is incorporated, in its entirety, by this reference.

TECHNICAL FIELD

The present disclosure relates generally to a method and system for handling bioadhesive materials, and more particularly, to methods and systems for storage, mixing and dispensing bioadhesive material for use in sealing tissue punctures.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,963 and 6,090,130, which are hereby incorporated in their entireties by this reference.

While there are a variety of prior art devices and techniques for closing such punctures, one primary problem is ensuring a complete seal of the puncture. One technique includes the use of a bioadhesive material to seal the puncture. Some types of bioadhesive materials must be activated prior to use, and should be activated just prior to use in order to avoid premature activation of the bioadhesive material that would affect its performance. The handling and activation of bioadhesive materials in the context of vascular and other tissue puncture closure devices present a number of challenges.

SUMMARY

One aspect of the present disclosure relates to a closure device operable to seal closed a puncture in a vessel. The closure device includes a delivery member, a sealing material applicator, and an expandable member. The delivery member is insertable through a tissue tract to the vessel puncture. The sealing material applicator is configured to supply a volume of sealing material to the delivery member and includes first and second multi-chamber devices and a valve assembly. Each chamber of the first and second multi-chamber devices holds a component of the sealing material, and operating the valve assembly permits mixing of at least some of the components prior to connecting the sealing material applicator to the delivery member. The expandable member is positionable within the vessel to temporarily seal closed the vessel puncture from within the vessel. The closure device is operable to deliver the sealing material from the sealing material applicator, through the delivery member, and to the tissue tract to seal closed the vessel puncture from outside the vessel.

The sealing material applicator may maintain separation of at least some of the components of the sealing material prior to connecting the sealing material applicator to the delivery member. The delivery member may be configured to mix the components together during delivery of the sealing material to the vessel puncture. The delivery member may include a hub, a delivery tube, and a guide sheath, wherein the sealing material applicator is connectable to the hub, the expandable member and delivery tube are delivered through the guide sheath to the vessel puncture, and the sealing material is delivered to the vessel puncture through the delivery tube. The first and second multi-chamber devices may be syringes having at least two chambers.

Another aspect of the present disclosure relates to a method of sealing a vessel puncture in a vessel. The method includes providing a closure device that includes a delivery member, a sealing material applicator, and an expandable member. The sealing material applicator includes first and second dual chamber applicators and a valve assembly, wherein each chamber of the first and second dual chamber applicators may hold a component of the sealing material. The method also includes operating the valve assembly to provide flow communication between the first and second dual chamber applicators, mixing some of the components in the sealing material applicator while maintaining separation of other components in the sealing material applicator, storing the mixed components in the first dual chamber applicator, connecting the first dual chamber applicator to the delivery member, expanding the expandable member within the vessel to temporarily seal closed the vessel puncture, and delivering the sealing material through the delivery member to the vessel puncture to seal closed the vessel puncture from outside of the vessel.

The method may also include retracting the expandable member and withdrawing the expandable member through the sealing material. The first dual chamber applicator may include a first chamber having a first component, and a second chamber having a second component, and the second dual chamber applicator may include a third chamber having a third component and a fourth chamber having a fourth component, wherein mixing at least some of the components includes mixing the first and third components and mixing the second and fourth components.

The method may include mixing all of the components during delivery of the sealing material through the delivery member. The first and third components may include different materials, and the second and fourth components may include the same material. Alternatively, the second and fourth materials may include different materials. The method may include detaching the first dual chamber applicator from the valve assembly prior to connecting the first dual chamber applicator to the delivery member. The first component may include a first polymer in a liquid state, the second component may include a second polymer in a liquid state, the third component may include a third polymer in a solid state, and the fourth component may include a fourth polymer in a solid state. The solid polymer is miscible in the liquid polymer with which it is mixed. Alternatively, one of the liquid state polymers may be, instead, a buffer solution. Further, alternatively, one of the solid polymers may instead be a liquid polymer such that a first and a third component may be the same liquid component or different liquid components. For example, the first and third liquid components may be the same liquid polymer or the same buffer solution, if the system requires a buffer solution. It is clear that various permutations of liquid and/or solid components are possible in forming the sealing material, dependent upon the nature of the sealing material.

Another aspect of the present disclosure relates to a sealing assembly that includes a sealing material applicator and a delivery device. The sealing material applicator includes first and second dual chamber syringes and a valve assembly. The first dual chamber syringe is configured to store a first sealing material component in a first chamber and a second sealing material component in a second chamber. The second dual chamber syringe is configured to store a third sealing material component in a third chamber and a fourth sealing material component in a fourth chamber. The valve assembly is operable to control fluid flow between the first and third chambers and the second and fourth chambers. The sealing material applicator is operable to mix the first and third sealing material components to create a first mixture, mix the second and fourth sealing material components to create a second mixture, and store the first and second mixtures in the first dual chamber syringe with the first and second mixtures separated until connecting the first dual chamber syringe to the delivery device. The first and second mixtures are mixed in the delivery device and delivered by the delivery device to a tissue puncture to seal closed the tissue puncture.

The first dual chamber syringe may be detachable from the valve assembly and attachable to the delivery device. The first and third sealing material components may include different active ingredients, and the second and fourth sealing material components may include the same active ingredients. Alternatively, the first and third sealing material components may include different active ingredients, and the second and fourth sealing material components may include different active ingredients. The first and third sealing material components may be in liquid and solid states, respectively, and the second sealing material component may be in a liquid state.

A further aspect of the present disclosure relates to a method of sealing a tissue puncture. The method includes providing a sealing material applicator having a valve assembly, a first device carrying a first sealing material component in a first chamber and a second sealing component in a second chamber, and a second device carrying a third sealing material component in third chamber and a fourth sealing material component in a fourth chamber. The method includes operating the valve assembly to permit flow communication between the first and third chambers and the second and fourth chambers, mixing the first and third components to create a first mixture and mixing the second and fourth components to create a second mixture, connecting a portion of the sealing material applicator to a delivery device, and mixing the first and second mixtures while delivering the first and second mixtures to a tissue puncture with the delivery device to seal closed the tissue puncture.

The method may also include temporarily sealing closed the tissue puncture internally with an expandable member prior to delivering the mixed first and second mixtures to the tissue puncture. The method may include retracting the expandable member and withdrawing the expandable member through the mixed first and second mixtures that have sealed closed the tissue puncture. The method may include storing the first and second mixtures in the first device, and detaching the first device from the valve assembly, and connecting the sealing material applicator to the delivery device includes connecting the first device to the delivery device.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 4 illustrates the tissue puncture closure device of FIG. 1 with the sealing material cured and the device prepared for withdrawal from the tissue puncture.

FIG. 5 illustrates the sealed tissue puncture after removal of the tissue puncture closure device.

FIG. 6 illustrates an example sealing material applicator with valves in a closed position in accordance with the present disclosure.

FIG. 7 illustrates the sealing material applicator of FIG. 6 with the valves in an open position.

FIG. 10 illustrates one of the multi-chamber sealing material devices of FIG. 7 carrying mixtures of components of the sealing material.

FIG. 11 illustrates another example sealing material applicator with valves in a closed position in accordance with the present disclosure.

Throughout the drawings, identical reference numbers designate similar, but not necessarily identical, elements.

DETAILED DESCRIPTION

Figure 1:
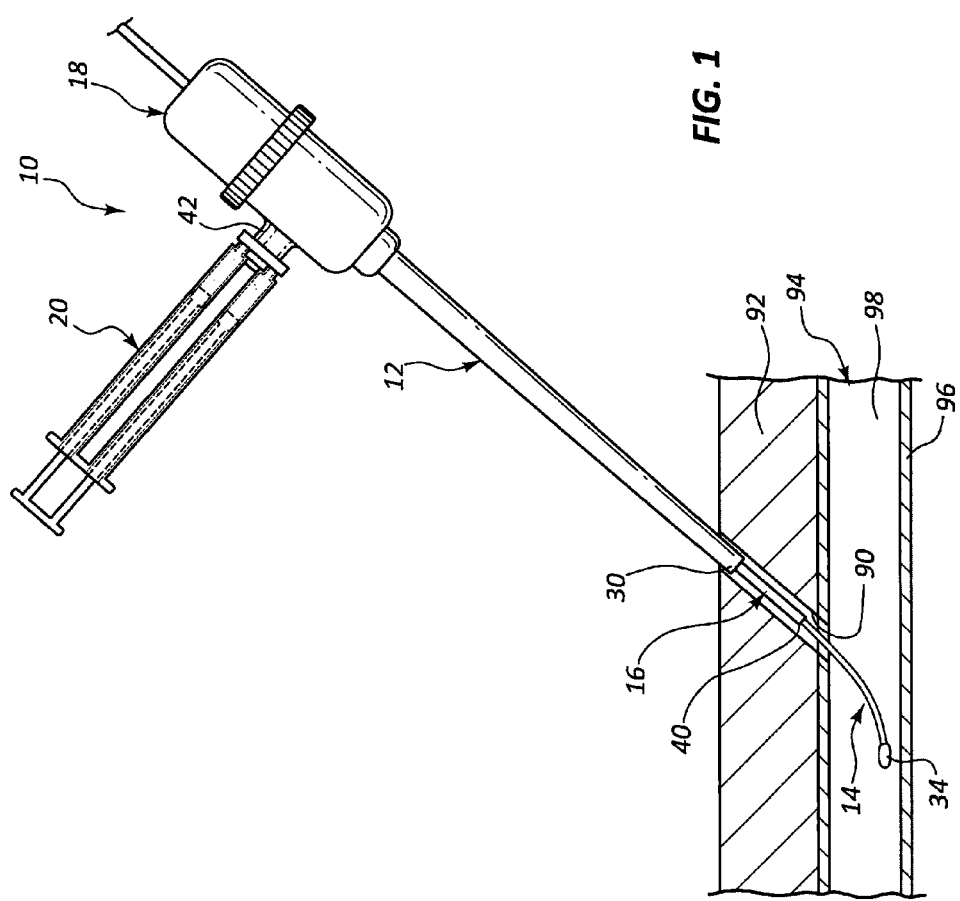
FIG. 1 illustrates an example tissue puncture closure device in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

The terms proximal and distal are used herein to refer to the relative positions of the components of an exemplary tissue puncture closure device 10. When used herein, proximal refers to a position relatively closer to the exterior of the body or closer to the surgeon. In contrast, distal refers to a position relatively further away from the surgeon or closer to the interior of the body.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising." The terms "biomaterial" or "composition" refer to a material intended to interface with biological systems to preferably evaluate, treat, or seal any tissue, organ or function of the body. Biomaterial refers to the complete material (precursor molecules plus all additives, base or solvents and bioactive agents, if any) at and after having reached and passed its gel-point. Composition refers to the complete material before having reached its gel-point. "Cross-linking" as used herein means the formation of covalent linkages. However, it may also refer to the formation of non-covalent linkages, such as ionic bonds, or combinations of covalent and non-covalent linkages. The term "gel" refers to the state of matter between liquid and solid. As such, a gel has some of the properties of a liquid (i.e., the shape is resilient and deformable) and some of the properties of a solid (i.e., the shape is discrete enough to maintain three dimensions on a two dimensional surface).

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the tissue puncture closure device 10 is illustrated in FIGS. 1-4, which is used to seal a percutaneous puncture 90 made through a tissue layer 92 and a vessel wall 96 of a vessel 94. Typically, the vessel 94 is a femoral artery in the groin region with a relatively large vessel passage or lumen 98 to facilitate improved locating of the vessel 94 and permitting a sufficiently large puncture to be made through the vessel wall 96 to carry out the procedure. Medical procedures that are typically performed through such a puncture include, for example, angioplasty and other procedures that pass a catheter or other type of probe into and along the vessel lumen 98.

When such a procedure is performed, an initial percutaneous puncture 90 with an appropriate needle is made through the tissue layer 92 and the vessel wall 96 and into the vessel lumen 98. A guide wire is installed through the percutaneous puncture 90, the needle is removed, and a guide sheath 12 of the tissue puncture closure device 10 is advanced over the guide wire and into the percutaneous puncture 90 to enlarge the puncture to permit easier access into the vessel 94. Other features of the tissue puncture closure device 10 may be advanced over the guide wire. The guide wire may be removed prior to operation of the tissue puncture closure device 10 to seal closed the percutaneous puncture 90.

The tissue puncture closure device 10 may include, in addition to the guide sheath 12, a temporary sealing component 14, a delivery tube 16, a hub 18, and a multi-chamber sealing material device 20 which carries a sealing material 24 for sealing closed the percutaneous puncture 90. Initially, the guide sheath 12 may extend through the percutaneous puncture 90 and into the vessel lumen 98 to enlarge or dilate the percutaneous puncture 90. The guide sheath 12 may be withdrawn until a distal end 30 is positioned at some location within the percutaneous puncture 90 or even withdrawn distally from the percutaneous puncture 90 after advancing other features of the tissue puncture closure device 10 into position (see FIG. 1). Any one or a combination of the guide sheath 12, delivery tube 16, and hub 18 may be referenced as a delivery device, delivery member, or delivery system that assists in delivering the sealing material 24 to the percutaneous puncture 90.

The temporary sealing component 14 may be inserted through the percutaneous puncture 90 until a portion is positioned within the vessel lumen 98. The temporary sealing component 14 may include a distal tip 34 and an expandable portion 36. The expandable portion contacts an inner surface of the vessel wall 96 when expanded (see FIGS. 2-3). The expandable portion 36 may move between an expanded position (see FIGS. 2 and 3) and a retracted position (see FIGS. 1 and 4). The expandable portion 36 may be expanded by an inflation fluid. Alternatively, the expandable portion 36 may be expanded using a mechanical structure covered by a membrane. The temporary sealing component 14 may be used to temporarily seal closed the percutaneous puncture 90 from within the vessel 94. In some arrangements, the distal tip 34 may be detachable within the sealing material 24 upon withdrawal of the temporary sealing component 14 to further seal closed percutaneous puncture 90 after removal of temporary sealing component 14.

The delivery tube 16 may be positioned within the percutaneous puncture 90. In some arrangements, the temporary sealing component 14 extends through the delivery tube 16. In other arrangements, the temporary sealing component 14 and delivery tube 16 are arranged in parallel extending through the guide sheath 12. The sealing material 24 carried by the multi-chamber sealing material device 20 may be delivered through the delivery tube 16 to the percutaneous puncture 90 (see FIGS. 3-4). The sealing material 24 may change from a liquid state to a gel or solid state to help retain the sealing material 24 within the percutaneous puncture 90 after removal of the temporary sealing component 14. The sealing material 24 may flow into and take a shape of the percutaneous puncture 90, thereby providing an improved seal for the percutaneous puncture 90 that is less likely to leak blood.

Figure 2:
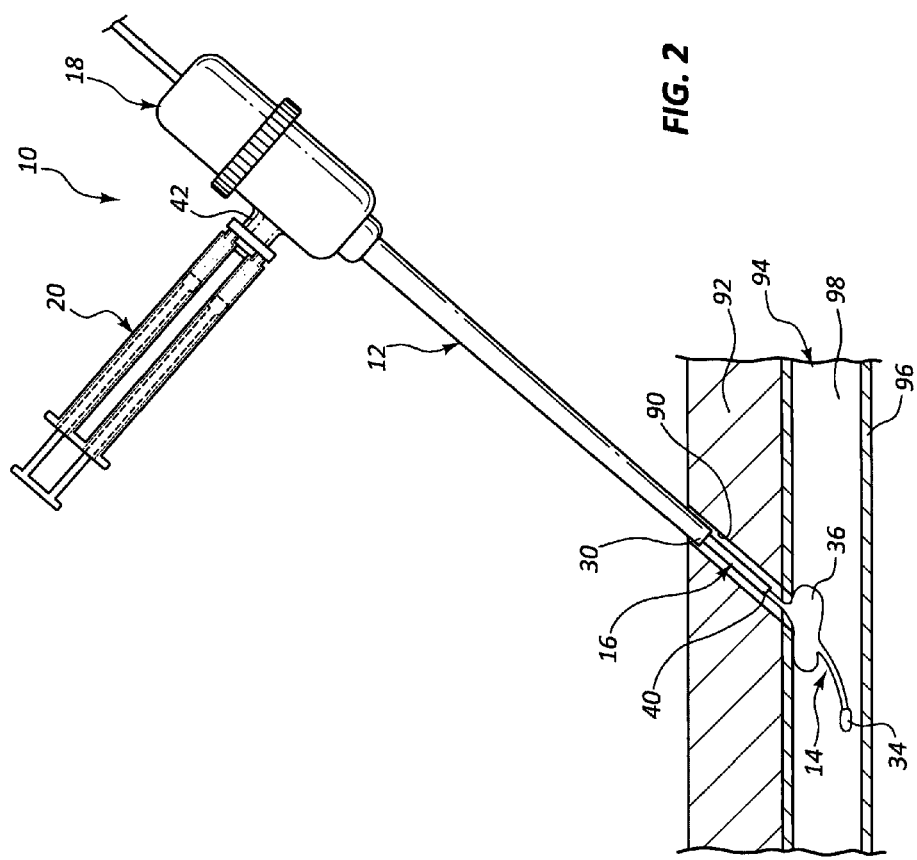
FIG. 2 illustrates the tissue puncture closure device of FIG. 1 with an expandable member expanded within the vessel to temporarily seal closed the tissue puncture.

In operation, the multi-chamber sealing material device 20 is connected to a delivery port 42 of the hub 18, and the guide sheath 12, temporary sealing component 14, and delivery tube 16 are positioned relative to the percutaneous puncture as shown in FIG. 1. In some arrangements, the valve assembly 26 remains connected to the multi-chamber sealing material device 20 and is interposed between the hub 18 and the multi-chamber sealing material device 20 to control flow of the sealing material 24. The expandable portion 36 of the temporary sealing component 14 is expanded to temporarily seal closed the percutaneous puncture 90 from within the vessel 94 as shown in FIG. 2.

Figure 3:
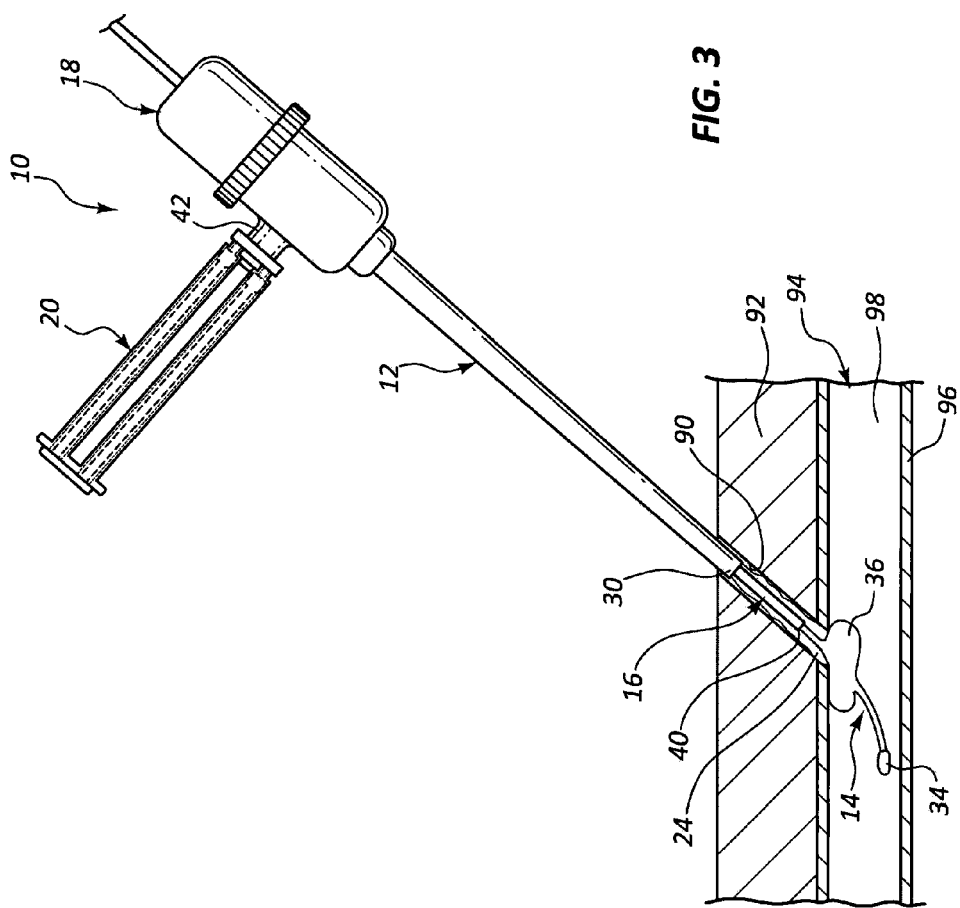
FIG. 3 illustrates the tissue puncture closure device of FIG. 1 delivering a sealing material to the vessel puncture.

The multi-chamber sealing material device 20 is operated to deliver the sealing material 24 through the delivery tube 16 to the percutaneous puncture 90 as shown in FIG. 3. The sealing material 24 is permitted to cure or at least partially cure so that the sealing material 24 does not flow into the vessel lumen 98 upon retracting the expandable portion 36 (see FIG. 4). The temporary sealing component 14 may be removed through the sealing material 24. The distal tip 34 may be lodged within the sealing material 24 in the empty cavity left behind upon removal of the temporary sealing component 14. The delivery tube 16 and guide sheath 12 may also then be removed from the percutaneous puncture 90. The sealing material 24 may continue to expand or flow within the percutaneous puncture 90 to fill any voids or cavities left behind upon removal of the guide sheath 12, temporary sealing component 14, and delivery tube 16 (see FIG. 5).

Referring now to FIGS. 6-7, the multi-chamber sealing material device 20 may be part of a sealing material applicator 80. The sealing material applicator 80 may include first and second multi-chamber sealing material devices 20, 22, and a valve assembly 26. Each of the first and second multi-chamber sealing material devices 20, 22 may include a housing 44 and a plunger assembly 46. Each of the housings 44 may include at least first and second chambers 48, 50, first and second outlet openings 52, 54, and a flange 56. The housings 44 may be integral with the first and second chambers 48, 50. Alternatively, at least one of the first and second chambers 48, 50 may be removable from the housing 44. In one example, the housing 44 acts as a bracket member that connects together multiple syringe-type devices that each carry a portion of the sealing material.

The plunger assembly 46 may include at least first and second plunger members 58, 60, seal portions 62, 64 associated with the first and second plunger members 58, 60, respectively, and a thumb applicator 66. The first and second plunger members 58, 60 may be used to expel and draw in components of the sealing material 24 into the first and second chambers 48, 50, respectively. The first and second plunger members 58, 60 may move in tandem upon application of an axial force to the thumb applicator 66.

The valve assembly 26 includes first and second actuators 28A,B and first and second sets of ports 29A,B. The first and second multi-chamber sealing material devices 20, 22 are connected to the first and second sets of ports 29A,B. The first and second actuators 28A,B operate between open and closed positions to control fluid flow between the first chambers 48 and the second chambers 50 of the first and second multi-chamber sealing material devices 20, 22.

Figure 8:
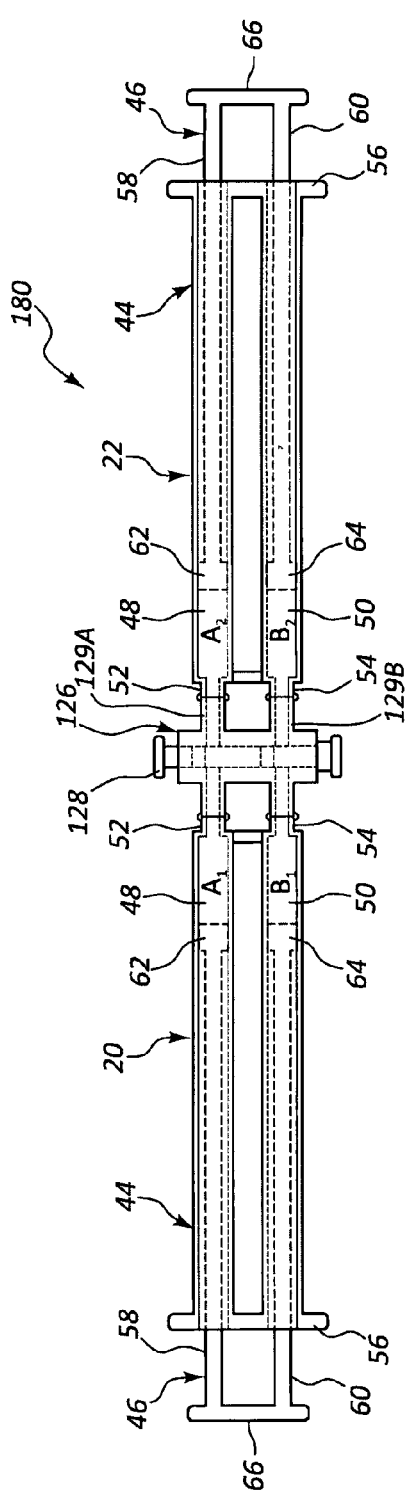
FIG. 8 illustrates another example sealing material applicator with valves in a closed position in accordance with the present disclosure.
Figure 9:
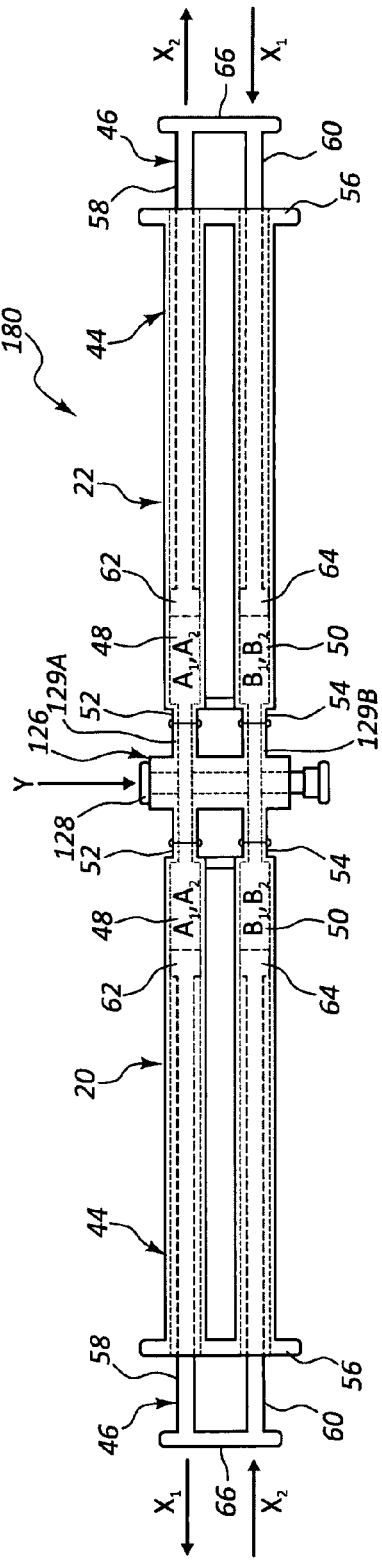
FIG. 9 illustrates the sealing material applicator of FIG. 8 with the valves in an open position.

The first and second actuators 28A,B of the valve assembly 26 may be configured as ball valves or other valve structures that operate using application of a rotational force. FIGS. 8-9 illustrate another valve assembly 126 having an actuator 128 that is actuated upon application of a linear force rather than a rotation force. The valve assembly 126 controls fluid flow through both sets of ports 129A,B with a single linear actuation force in a lateral direction Y. In contrast, the valve assembly 26 includes separate first and second actuators 28A,B which independently control fluid flow through each of the sets of ports 29A,B. Many other types of actuators and valve assemblies may be used to provide controlled of fluid flow between the first and second multi-chamber sealing material devices 20, 22.

Typically, when the valve assemblies 26, 126 are closed as shown in FIGS. 6 and 8, the plunger assemblies 46 are unable to move because of the fluid tight connection with the valve assembly 26, 126. However, once the valve assemblies 26, 126 are open as shown in FIGS. 7 and 9, the plunger assemblies 46 can be operated in the $X_1$, $X_2$ directions to mix the contents held in the first and second chambers 48, 50 of the first and second multi-chamber sealing material devices 20, 22.

In one example, the first multi-chamber sealing material device 20 includes components $A_1$, $B_1$ in the first and second chambers 48, 50 (see FIG. 6), and the second multi-chamber sealing material device 22 includes components $A_2$, $B_2$ in the first and second chambers 48, 50. Actuating the plunger assemblies 46 as shown in FIG. 7 mixes the components $A_1$, $A_2$ together to form a first mixture, and mixes the components $B_1$, $B_2$ to form a second mixture. The first and second mixtures may be stored in the first and second chambers 48, 50 of one of the first and second multi-chamber sealing material devices 20, 22 as shown in FIG. 10. The multi-chamber sealing material device carrying the first and second mixtures may then be connected to the tissue puncture closure device 10 to provide a supply of sealing material for delivery to the percutaneous puncture 90. The first and second mixtures may remain separated until after the multi-chamber sealing material device is connected to the hub 18 of the tissue puncture closure device 10. In some arrangements, the first and second mixtures held by the multi-chamber sealing material device may remain separated until delivery of the first and second mixtures, at which point the first and second mixtures are mixed together during delivery through the delivery tube 16 (or at another location within the tissue puncture closure device 10 such as the hub 18) to the percutaneous puncture 90.

In one example, the component $A_1$ includes a first polymer component and the component $A_2$ contains a second polymer component, which when combined together create a cross-linked polymer. At least one of the components $B_1$, $B_2$ may include an activator or buffer, which when combined with the mixture of $A_1$, $A_2$ creates an activated polymer that begins to cure. Typically, the mixture $A_1$ $A_2$ is activated just prior to delivery of the sealing material to the percutaneous puncture 90. Thus, there may be advantages to providing a multi-chamber sealing material device that maintains separation of the mixtures $A_1$, $A_2$ and $B_1$, $B_2$ until delivery of the sealing material through the delivery tube 16 to the percutaneous puncture 90.

In some examples, the components $A_1$, $A_2$ have a different physical state (e.g., $A_1$ includes a liquid or gel with an active ingredient dissolved therein, and $A_2$ is a solid that is dissolved in $A_1$ by mixing). The components $B_1$, $B_2$ may also have different physical properties such as liquid, gel or solid. Preferably, at least one of the components in the mixture $A_1$, $A_2$ and the mixture $B_1$, $B_2$ is a liquid or gel to promote effective mixing and dissolving of the other component.

Figure 12:
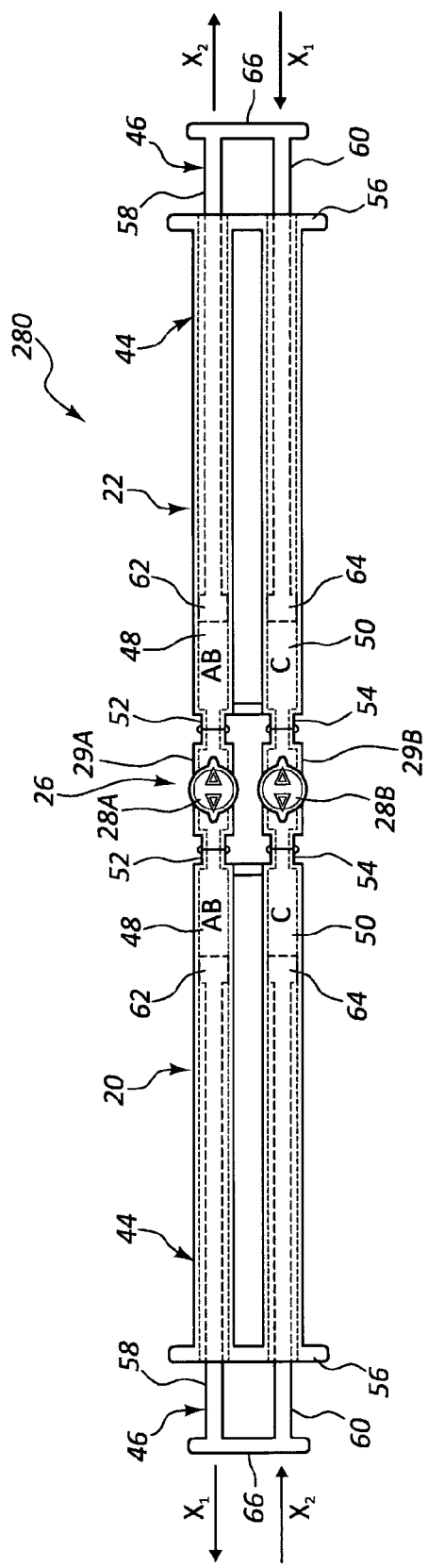
FIG. 12 illustrates the sealing material applicator of FIG. 11 with the valves in an open position.
Figure 13:
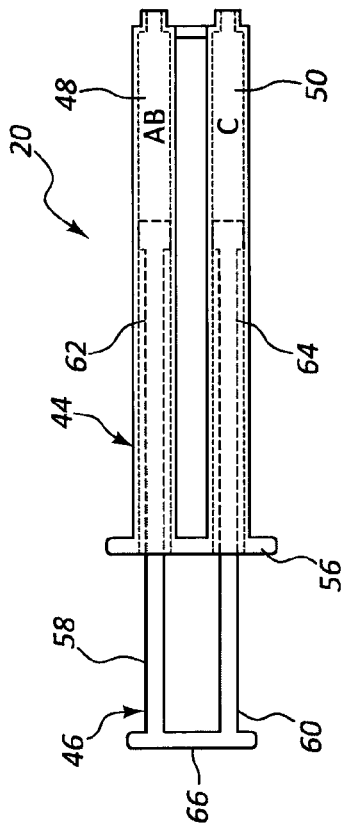
FIG. 13 illustrates one of the multi-chamber sealing material devices of FIG. 12 carrying mixtures of the sealing material components.

Referring now to FIGS. 11-13, another example sealing material applicator 280 includes first and second multi-chamber sealing material devices 20, 22 that include components A, C and B, C, respectively. The mixture is created by a sealing material applicator 280 that includes a mixture having components A, B and a mixture that includes component C alone (see FIG. 13). In some arrangements, one of the first and second multi-chamber sealing material devices 20, 22 includes the component C and the other does not include component C (i.e., is left empty rather than also carrying the component C). In other arrangements, the components C in the first and second multi-chamber sealing material devices 20, 22 may be in different physical states (i.e., liquid and solid), but have the same active ingredient. Many other variations may be utilized with the number, physical state, and types of components handled by the sealing material applicators. In some arrangements, three or more chambers may be included in each of the first and second multi-chamber sealing material devices, and different variations of the type of component held in each chamber are possible.

In one example (see FIGS. 6-7), the component $A_1$ may include a first polymer in a liquid state, the component $B_1$ may include a second polymer in a liquid state, the component $A_2$ may include a third polymer in a solid state, and the component $B_2$ may include a fourth polymer in a solid state. A solid polymer is miscible in the liquid polymer with which it is mixed. Alternatively, one of the liquid state polymers may be, instead, a buffer solution. Further, alternatively, one of the solid polymers may instead be a liquid polymer such that, for example, the components $B_1$, $B_2$ may be the same liquid component or different liquid components. In another example, the components $A_1$, $A_2$ or $B_1$, $B_2$ may be the same liquid polymer or the same buffer solution, if the system requires a buffer solution. Various permutations of liquid and/or solid components are possible in forming the sealing material, dependent upon the nature of the sealing material.

The sealing materials and sealing material applicators disclosed herein may be used with other types of tissue puncture closure devices besides the tissue puncture closure device 10 shown with reference to FIGS. 1-4. The sealing materials may be used in other applications besides sealing closed a tissue puncture such as a puncture in a vessel wall or a puncture in the tissue leading to a vessel. The need to restrict flow of sealing material into the vessel provides some unique challenges in the context of sealing closed a percutaneous puncture in a vessel wall.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A closure device operable to seal a vessel puncture in a vessel, the closure device comprising:
a delivery member insertable through a tissue tract to the vessel puncture;
a sealing material applicator configured to supply a volume of sealing material to the delivery member, the sealing material applicator including first and second multi-chamber devices and a single valve member, each chamber of the first and second multi-chamber devices holding a component of the sealing material, the single valve member being positioned within a valve housing having tubular ports extending away from an outer surface of the valve housing, wherein the single valve member is operated by applying a linear actuation force within the valve housing to permit simultaneous mixing of components held in first and second chambers of the first multi-chamber device with components held in first and second chambers of the second multi-chamber device, respectively, prior to connecting the sealing material applicator to the delivery member;
an expandable member positionable within the vessel to temporarily seal the vessel puncture from within the vessel;
wherein the closure device is operable to deliver the sealing material from the sealing material applicator, through the delivery member and to the tissue tract to seal the vessel puncture from outside the vessel.

2. The closure device of claim 1, wherein the sealing material applicator maintains separation of at least some of the components prior to connecting the sealing material applicator to the delivery member.

3. The closure device of claim 1, wherein the delivery member is configured to mix the components together during delivery of the sealing material to the vessel puncture.

4. The closure device of claim 1, wherein the delivery member includes a hub, a delivery tube, and a guide sheath, wherein the sealing material applicator is connectable to the hub, the expandable member and delivery tube are delivered through the guide sheath to the vessel puncture, and the sealing material is delivered to the vessel puncture through the delivery tube.

5. The closure device of claim 1, wherein the first and second multi-chamber devices are syringes having at least two chambers.

6. A method of sealing a vessel puncture in a vessel, comprising:
providing a closure device that includes a delivery member, a sealing material applicator, and an expandable member, the sealing material applicator including a first dual chamber applicator having first and second chambers, a second dual chamber applicator having third and fourth chambers, and a valve assembly, each chamber of the first and second dual chamber applicators holding a component of the sealing material, the valve assembly comprising a single valve member positioned within a valve housing, the valve housing having tubular ports extending away from an external surface of the valve housing and connecting to the first and second dual chamber applicators, respectively;
operating the single valve member by applying a linear force to simultaneously provide flow communication between the first and third chambers and between the second and fourth chambers;
mixing the components in the first and third chambers and mixing the components in the second and fourth chambers while maintaining separation of the components in the first and third chambers from the components in the second and fourth chambers;
storing the mixed components in the first dual chamber applicator;
connecting the first dual chamber applicator to the delivery member;
expanding the expandable member within the vessel to temporarily seal the vessel puncture;
delivering the sealing material through the delivery member to the vessel puncture to seal the vessel puncture from outside of the vessel.

7. The method of claim 6, further comprising retracting the expandable member and withdrawing the expandable member through the sealing material.

8. The method of claim 6, wherein the first chamber holds a first component, the second chamber holds a second component, the third chamber holds a third component, and the fourth chamber holds a fourth component.

9. The method of claim 8, wherein the first and third components comprise different materials, and the second and fourth components comprise the same material.

10. The method of claim 6, further comprising mixing all of the components during delivery of the sealing material through the delivery member.

11. The method of claim 6, further comprising detaching the first dual chamber applicator from the valve assembly prior to connecting the first dual chamber applicator to the delivery member.

12. The method of claim 6, wherein the valve member is operated in a lateral direction.

13. The method of claim 6, wherein the valve member is operated in a linear motion.

14. A sealing assembly, comprising:
a sealing material applicator, comprising:
a first dual chamber syringe configured to store a first sealing material component in a first chamber and a second sealing material component in a second chamber;

a second dual chamber syringe configured to store a third sealing material component in a third chamber and a fourth sealing material component in a fourth chamber;

a valve assembly, the valve assembly comprising single valve member and a valve housing, the single valve member being operable in a lateral direction within the valve housing by application of a linear force to simultaneously control fluid flow between the first and third chambers and between the second and fourth chambers, the valve housing having a plurality of tubular ports extending away from an external surface of the valve housing;

a delivery device;

wherein the sealing material applicator is operable to mix the first and third sealing material components to create a first mixture, and mix the second and fourth sealing material components to create a second mixture, and store the first and second mixtures in the first dual chamber syringe with the first and second mixtures separated until connecting the first dual chamber syringe to the delivery device, wherein the first and second mixtures are mixed in the delivery device and delivered by the delivery device to a tissue puncture to seal the tissue puncture.

15. The sealing assembly of claim 14, wherein the first dual chamber syringe is detachable from the single valve member and attachable to the delivery device.

16. The sealing assembly of claim 14, wherein the first and third sealing material components comprise different active ingredients, and the second and fourth sealing material components comprise the same active ingredients.

17. The sealing assembly of claim 14, wherein the first and third sealing material components comprise different active ingredients, and the second and fourth sealing material components comprise different active ingredients.

18. The sealing assembly of claim 14, wherein the first and third sealing material components are in liquid and solid states, respectively, and the second sealing material component is in a liquid state.

19. A method of sealing a tissue puncture, comprising:

providing a sealing material applicator having a valve assembly, the valve assembly having a single valve member positioned within a valve housing, the sealing material applicator having a first device carrying a first sealing material component in a first chamber and a second sealing component in a second chamber and having a second device carrying a third sealing material component in a third chamber and a fourth sealing material component in a fourth chamber;

operating the single valve member by applying a linear force to simultaneously permit flow communication between the first and third chambers and between the second and fourth chambers through tubular ports of the valve assembly, the tubular ports extending away from an external surface of the valve housing;

mixing the first and third components to create a first mixture and mixing the second and fourth components to create a second mixture;

connecting the sealing material applicator to a delivery device;

mixing the first and second mixtures while delivering the first and second mixtures to a tissue puncture with the delivery device to seal the tissue puncture.

20. The method of claim 19, further comprising temporarily sealing the tissue puncture internally with an expandable member prior to delivering the mixed first and second mixtures to the tissue puncture.

21. The method of claim 20, further comprising retracting the expandable member and withdrawing the expandable member through the mixed first and second mixtures that have sealed the tissue puncture.

22. The method of claim 19, further comprising storing the first and second mixtures in the first device, and detaching the first device from the valve member, and connecting the sealing material applicator to the delivery device includes connecting the first device to the delivery device.

23. The method of claim 19, wherein the valve member is operated linearly in a lateral direction.

* * * * *